(12) United States Patent
Hieshima

(10) Patent No.: US 6,361,547 B1
(45) Date of Patent: Mar. 26, 2002

(54) EMBOLIC COIL HYDRAULIC DEPLOYMENT SYSTEM

(75) Inventor: Grant Hieshima, Huntington Beach, CA (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/641,552

(22) Filed: Aug. 17, 2000

Related U.S. Application Data

(63) Continuation of application No. 09/177,848, filed on Oct. 22, 1998, now Pat. No. 6,113,622.
(60) Provisional application No. 60/077,468, filed on Mar. 10, 1998.

(51) Int. Cl.[7] ............................................. A61M 29/00
(52) U.S. Cl. ........................................ 606/200; 606/108
(58) Field of Search ................ 606/200, 108, 606/198, 191, 206–194, 127; 604/14, 103.03, 104–106

(56) References Cited

U.S. PATENT DOCUMENTS

| | | |
|---|---|---|
| 2,853,070 A | 9/1958 | Julliard |
| 3,353,718 A | 11/1967 | McLay |
| 4,512,338 A | 4/1985 | Balko et al. |
| 4,743,230 A | 5/1988 | Nordquest |
| 4,832,692 A | 5/1989 | Box et al. |
| 4,919,121 A | 4/1990 | Rydell et al. |
| 4,994,069 A | 2/1991 | Ritchart et al. |
| 4,994,071 A | 2/1991 | MacGregor |
| 5,108,407 A | 4/1992 | Geremia et al. |
| 5,122,136 A | 6/1992 | Guglielmi et al. |
| 5,137,514 A | 8/1992 | Ryan |
| 5,167,624 A | 12/1992 | Butler et al. |
| 5,168,757 A | 12/1992 | Rabenau et al. |
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,304,195 A | 4/1994 | Twyford, Jr. et al. |
| 5,312,415 A | 5/1994 | Palermo |
| 5,334,210 A | 8/1994 | Gianturco |
| 5,336,183 A | 8/1994 | Greelis et al. |
| 5,342,304 A | 8/1994 | Tacklind et al. |
| 5,350,397 A | 9/1994 | Palermo et al. |
| 5,382,259 A | 1/1995 | Phelps et al. |
| 5,403,292 A | 4/1995 | Ju |
| 5,443,478 A | 8/1995 | Purdy |
| 5,470,317 A | 11/1995 | Cananzey et al. |

(List continued on next page.)

FOREIGN PATENT DOCUMENTS

| | | |
|---|---|---|
| EP | 0 717 969 A | 6/1996 |
| WO | WO 98/02100 | 1/1998 |

OTHER PUBLICATIONS

Brochure entitled, "Guglielmi Detachable Coils," by Boston Scientific Label of IDC–18 Interlocking Detachable Coil by Target Therapeutics, Inc.
Brochure entitled, "Detachable Coil System," by Cook.
Brochure entitled, "Basix25™ Inflation Device," by Merit Medical System, Inc.
Brochure entitled, "MonarchAP® Inflation Device," by Merit Medical Systems, Inc. Label of B. Braun Inflation Device Kit by B. Braun Medical Inc.

*Primary Examiner*—Kevin Truong
(74) *Attorney, Agent, or Firm*—Henry W. Collins

(57) ABSTRACT

A medical device for placing an embolic coil at a preselected location within a vessel comprising a positioning catheter having a distal tip for retaining the embolic coil which when pressurized with a fluid expands outwardly to release the coil at the preselected position.

23 Claims, 2 Drawing Sheets

U.S. PATENT DOCUMENTS

| | | |
|---|---|---|
| 5,551,954 A | 9/1996 | Buscemi et al. |
| 5,578,074 A | 11/1996 | Mirigian |
| 5,582,619 A | 12/1996 | Ken |
| 5,601,600 A | 2/1997 | Ton |
| 5,609,608 A | 3/1997 | Benett et al. |
| 5,647,847 A | 7/1997 | Lafontaine et al. |
| 5,690,667 A | 11/1997 | Gia |
| 5,772,668 A | 6/1998 | Summers et al. |
| 5,853,418 A | 12/1998 | Ken et al. |
| 5,928,226 A * | 7/1999 | Guglielmi et al. .......... 606/108 |
| 5,984,929 A * | 11/1999 | Bashiri et al. .............. 606/108 |
| 6,063,100 A * | 5/2000 | Diaz et al. .................. 606/191 |
| 6,117,142 A * | 9/2000 | Goodson et al. ............ 606/108 |
| 6,183,491 B1 * | 2/2001 | Lulo .......................... 606/191 |

\* cited by examiner

EMBOLIC COIL HYDRAULIC DEPLOYMENT SYSTEM

This application is a continuation of U.S. application Ser. No. 09/177,848 filed Oct. 22, 1998, now U.S. Pat. No. 6,113,622, which is provisional application 60/077,468 filed Mar. 10, 1998.

BACKGROUND OF THE INVENTION

1. Field of the Invention

The present invention relates to a medical device for placing an embolic coil at a preselected location within a vessel of the human body, and more particularly, relates to a catheter having a distal tip for retaining the embolic coil in order to transport the coil to a preselected position within the vessel and a control mechanism for releasing the embolic coil at the preselected position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected position within vessel of the human body in order to treat aneurysms or alternatively to occlude the blood vessel at the particular location.

Coils which are placed in vessels may take the form of helically wound coils, or alternatively, may be random wound coils, coils wound within other coils or many other such coil configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Coverings." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, embolic coils have been placed within the distal end of the catheter and when the distal end of the catheter is properly positioned the coil may then be pushed out of the end of the catheter with, for example a guidewire, to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to be detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate element which extends throughout the length of the catheter with the resulting stiffness of the catheter.

SUMMARY OF THE INVENTION

The present invention is directed toward a vascular occlusive coil deployment system for use in placing an embolic coil at a preselected site within a vessel which includes an elongated, flexible catheter having a distal tip for retaining the coil so that the coil may be moved to the preselected position within the vessel. The catheter has a lumen which extends therethrough the length of the catheter and also includes a distal end which is formed of a material having a durometer such that when a fluid pressure of about 300 pounds per square inch (psi) is applied to the interior of the catheter, the walls of the distal tip expand outwardly, or radially, to thereby increase the lumen of the distal tip of the catheter. The proximal end of the embolic coil is placed into the lumen of the distal tip of the catheter and is retained by the distal tip of the catheter. A hydraulic injector, such as a syringe, is coupled to the proximal end of the catheter for applying a fluid pressure to the interior of the catheter. When the coil is placed at a desired position within a vessel, fluid pressure is then applied to the interior of the catheter by the hydraulic injector to thereby cause the walls of the distal tip to expand outwardly to thereby release the coil for placement in the vessel.

In accordance with another aspect of the present invention, the flexible catheter is comprised of a proximal section and a relatively short distal section. The proximal section is formed of a material which is sufficiently flexible to be passed through the vasculature of the human body and is of a durometer which essentially resists outward expansion when a fluid pressure on the order of about 300 psi is applied to the interior of the catheter. The distal section of the catheter is formed of a material which is also sufficiently flexible to be passed through the vasculature of the body, yet is of a durometer which is significantly lower than the durometer of the proximal section and exhibits the property of expanding outwardly, or radially, when such a fluid pressure is applied to the interior of the catheter to thereby permit the release of the embolic coil.

In accordance with still another aspect of the present invention, the distal section of the catheter has a durometer in a range of between about 25 D and 55 D.

In still another aspect of the present invention, the embolic coil is comprised of a helical coil having a proximal end, a distal end, and a lumen extending therethrough. A seal plug is disposed within the lumen of the proximal end of the coil in fluid-tight engagement. The proximal end of the coil is disposed in a fluid-tight engagement within the lumen of the distal section of the catheter and is retained by the lumen of the catheter for subsequent release.

In another aspect of the present invention, the hydraulic injector for applying a fluid pressure to the interior of the catheter takes the form of a syringe which is coupled to the proximal end of the catheter for, upon movement of the piston, creating a fluid pressure which is applied to the interior of the catheter to thereby cause the release of the embolic coil.

In accordance with another aspect of the present invention, the embolic coil may take the form of other types of implantable devices, such as a vascular filter.

In another aspect of the present invention, there is provided a method for placing an embolic coil with a selected site within a vessel of the body comprising the steps of advancing a catheter through the vasculature of the body to place an embolic coil which is retained within the lumen of the distal tip of the catheter to a preselected site, applying a fluid pressure to the interior of the catheter to thereby cause the distal tip of the catheter to expand radially outwardly to release the embolic coil at the preselected site, and withdrawing the catheter from the vasculature system.

These aspects of the invention and the advantages thereof will be more clearly understood from the following description and drawings of a preferred embodiment of the present invention:

DESCRIPTION OF A PREFERRED EMBODIMENT

Figure 1:
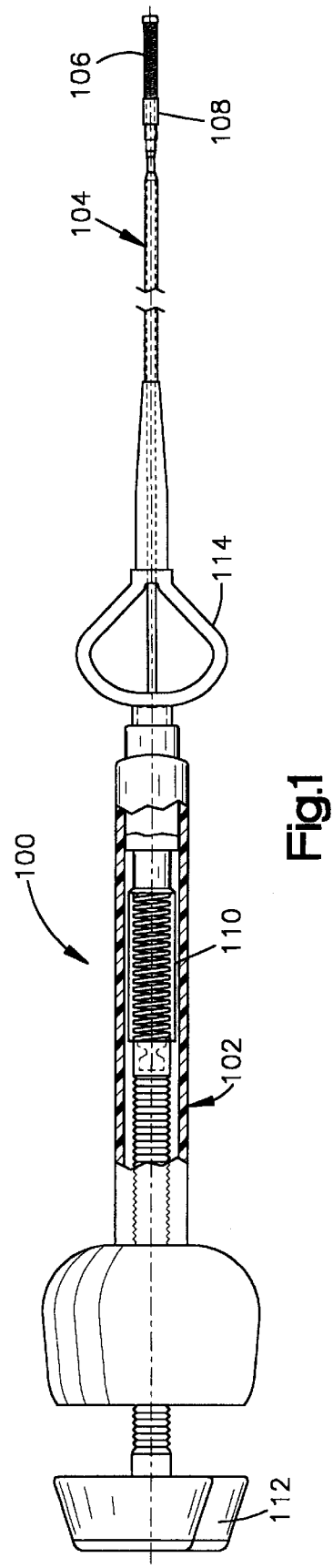
FIG. 1 is an enlarged, partial sectional view of the hydraulic vascular occlusive coil deployment system of the present invention.

FIG. 1 generally illustrates the vascular occlusive coil deployment system 100 which is comprised of a hydraulic injector or syringe 102, coupled to the proximal end of a catheter 104. An embolic coil 106 is disposed within the lumen of the distal end 108 of the catheter. The proximal end of the coil 106 is tightly held within the lumen of the distal section 108 of the catheter 104 until the deployment system is activated for release of the coil.

As may be seen, the syringe 102 includes a threaded piston 110 which is controlled by a handle 112 for infusing fluid into the interior of the catheter 104. Also as illustrated, the catheter 104 includes a winged hub 114 which aids in the insertion of the catheter into the vascular system of the body.

Figure 2:
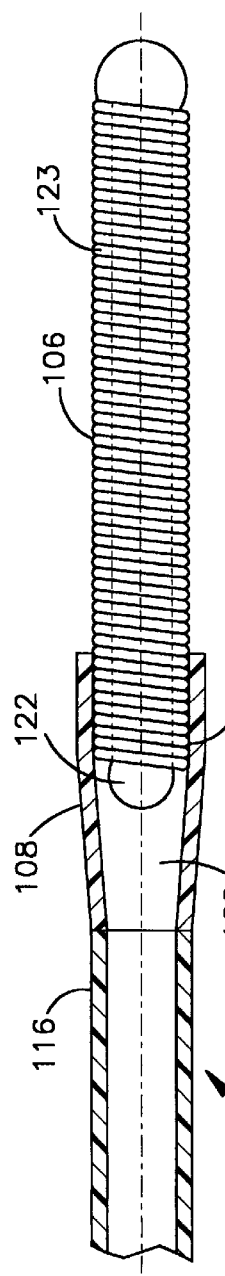
FIG. 2 is an enlarged partially sectional view showing the distal end of the coil deployment system prior to deployment of the coil.

FIG. 2 illustrates in more detail the distal end of the catheter 104. The catheter 104 includes a proximal section 116 and the distal section 108. The proximal section 118 of the embolic coil 106 is disposed within the distal section 108 of the catheter and is tightly held within the lumen 120 of this distal section 108 prior to release of the coil. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a weld bead or seal plug 122 which is disposed in a lumen 123 which lumen extends throughout the length of the coil 106. The seal plug 122 serves to prevent the flow of fluid through the lumen of the coil 106 so that when the coil 106 is placed in fluid-tight engagement with the lumen 120 the coil serves to provide a fluid-tight seal at the distal end of the catheter 104.

Adjacent turns of the coil 106 at the proximal end 118 of the coil are preferably continuously welded together so that the welded turns of the coil in conjunction with the plug seal 122 provide a generally unitary structure which serves to plug or seal the distal end of the catheter in a fluid tight relationship.

Preferably, the proximal section 116 and the distal section 108 of the catheter 104 are formed of materials having different durometers. The proximal section 116 is preferably formed of Pebax material having a durometer in a range of about 62 D to 75 D. The proximal section is sufficiently flexible to transverse the vasculature of the human body, but is sufficiently rigid such that when a fluid pressure of approximately 300 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 300 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25 D and 55 D with a durometer of 40 D being the preferred durometer.

Figure 3:
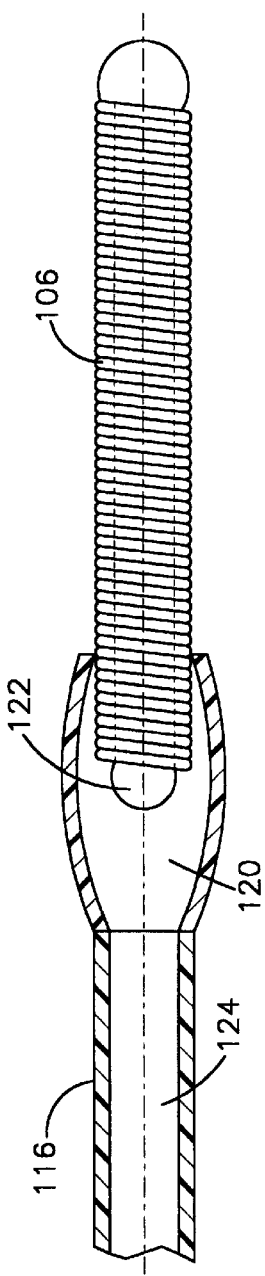
FIGS. 3 and 4 illustrate the sequential steps in the radial expansion of the distal tip of the coil deployment system as the embolic coil is released.
Figure 4:
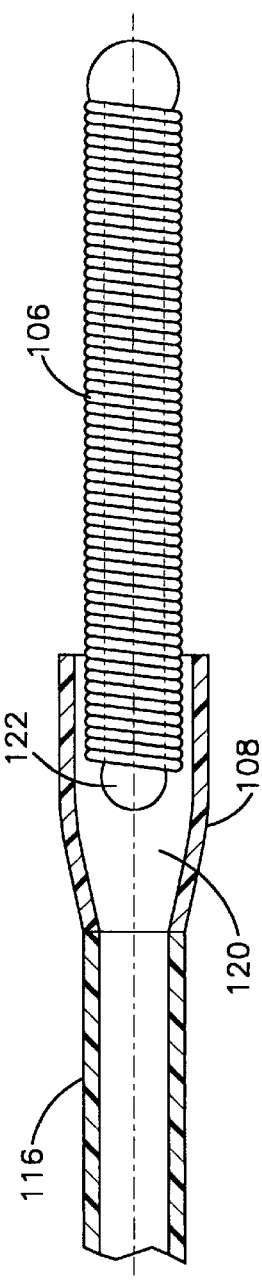

FIGS. 3 and 4 generally illustrate the coil release mechanism in action for the vascular occlusive catheter deployment system. More particularly, as shown in FIG. 3, when a hydraulic pressure is applied to the interior 124 of the catheter 104 the relatively low durometer distal section 108 of the catheter begins to expand radially, much as a balloon expands during the process of inflation. As the distal section 108 continues to expand radially there comes a point as illustrated in FIG. 4 in which the coil 106 becomes disengaged from the lumen of the distal section 108 and the coil is then released from the catheter and is deployed at that location within the vessel.

Figure 5:
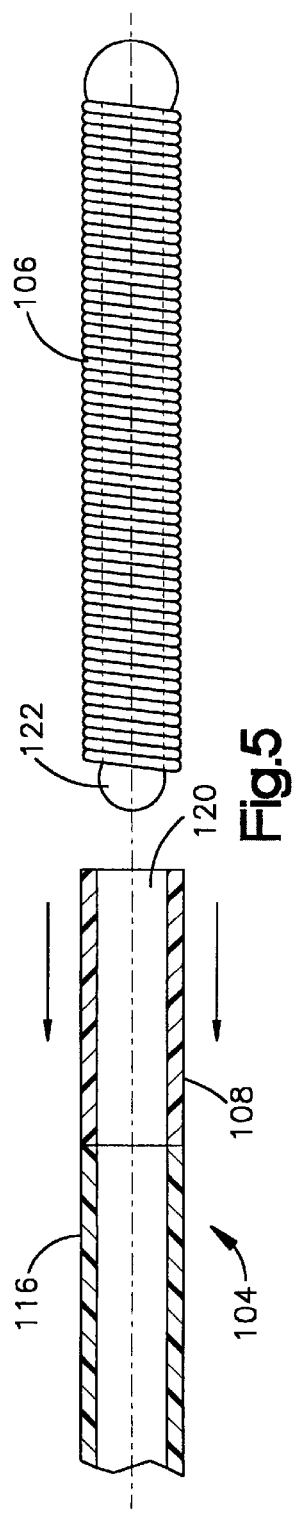
FIG. 5 illustrates the distal tip of the coil deployment system after release of the embolic coil.

As illustrated in FIG. 5, when the coil 106 has been released from the catheter 104 the catheter may then be withdrawn leaving the coil positioned at the desired site.

With the vascular occlusive coil deployment system of the present invention it is possible to place an embolic coil very precisely at a desired location within a vessel. Once the coil has been placed in that location by use of the catheter, the catheter may be activated by applying a hydraulic pressure to the interior of the catheter to thereby cause the catheter to release the coil and deposit the coil very accurately at the desired location.

As is apparent, there are numerous modifications of the preferred embodiment described above which will be readily apparent to one skilled in the art, such as many variations and modifications of the coil including numerous coil winding configurations, or alternatively other types of implant devices, such as a vascular filter. Also, there are obviously variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims which follow.

That which is claimed is:

1. A vasoocclusive coil deployment system for use in placing a coil at a preselected site within a vessel comprising:
    an elongated flexible catheter having a lumen extending therethrough and having a proximal section and a distal section, said distal section of the catheter being formed of a material having a durometer which exhibits the characteristic that when a fluid pressure is applied to the lumen of the catheter the walls of the distal section of the catheter expand outwardly;
    an embolic coil being disposed in fluid-tight engagement within the lumen of the distal section of the catheter; and,
    a source of fluid pressure coupled to the proximal section of the catheter for upon actuation applying fluid pressure to the lumen of the catheter to thereby cause the distal section of the catheter to expand outwardly to thereby release the embolic coil.

2. A vasoocclusive coil deployment system as defined in claim 1, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the catheter, the distal section is formed of a material which is also sufficiently flexible to be passed through the vasculature of the body and is of a durometer which is substantially lower than the durometer of the proximal section.

3. A vasoocclusive coil deployment system as defined in claim 2, wherein the distal section of the catheter is formed of a polymer having a durometer in a range of between about 25 D and 55 D.

4. A vasoocclusive coil deployment system as defined in claim 2, wherein the distal section of the catheter has a durometer of about 40 D.

5. A vasoocclusive coil deployment system as defined in claim 3, wherein the embolic coil is comprised of a helical coil having a proximal end, a distal end and a lumen extending therethrough, a seal plug is disposed in fluid-tight engagement within the lumen at the proximal end of the coil and the proximal end of the coil is disposed within the lumen of the distal section of the catheter.

6. A vasoocclusive coil deployment system as defined in claim 3, wherein said proximal section of said catheter is formed of a polymer having a durometer in a range of 62 D to 75 D.

7. A vasoocclusive coil deployment system for use in placing a coil at a preselected site within a vessel comprising:
    an elongated flexible catheter having a lumen extending therethrough and having a proximal section and a distal section, said distal section of the catheter being formed of a material having a durometer which exhibits the characteristic that when a fluid pressure is applied to the lumen of the catheter the walls of the distal section of the catheter expand outwardly;
    an embolic coil being disposed in fluid-tight engagement within the lumen of the distal section of the catheter; and,
    a connector coupled to the proximal section of the catheter adapted to be connected to a source of fluid pressure which when applied through the connector to the lumen of the catheter causes the distal section of the catheter to expand outwardly to thereby release the embolic coil.

8. A vasoocclusive coil deployment system as defined in claim 7, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the catheter, the distal section is formed of a material which is also sufficiently flexible to be passed through the vasculature of the body and is of a durometer which is substantially lower than the durometer of the proximal section.

9. A vasoocclusive coil deployment system as defined in claim 8, wherein the distal section of the catheter is formed of a polymer having a durometer in a range of between about 25 D and 55 D.

10. A vasoocclusive coil deployment system as defined in claim 8, wherein the distal section of the catheter has a durometer of about 40 D.

11. A vasoocclusive coil deployment system as defined in claim 9, wherein the embolic coil is comprised of a helical coil having a proximal end, a distal end and a lumen extending therethrough, a seal plug is disposed in fluid-tight engagement within the lumen at the proximal end of the coil and the proximal end of the coil is disposed within the lumen of the distal section of the catheter.

12. A vasoocclusive coil deployment system as defined in claim 9, wherein said proximal section of said catheter is formed of a polymer having a durometer in a range of 62 D to 75 D.

13. An implant device deployment system for use in placing a coil at a preselected site within a vessel comprising:
    an elongated flexible catheter having a lumen extending therethrough and having a proximal section and a distal section, said distal section of the catheter being formed of a material having a durometer which exhibits the characteristic that when a fluid pressure is applied to the lumen of the catheter the walls of the distal section of the catheter expand outwardly;

an implant device being disposed in fluid-tight engagement within the lumen of the distal section of the catheter; and, a source of fluid pressure coupled to the proximal section of the catheter for upon actuation applying fluid pressure to the lumen of the catheter to thereby cause the distal section of the catheter to expand outwardly to thereby release the implant device.

14. An implant device deployment system as defined in claim 13, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the catheter, the distal section is formed of a material which is also sufficiently flexible to be passed through the vasculature of the body and is of a durometer which is substantially lower than the durometer of the proximal section.

15. An implant device deployment system as defined in claim 14, wherein the distal section of the catheter is formed of a polymer having a durometer in a range of between about 25 D and 55 D.

16. An implant device deployment system as defined in claim 14, wherein the distal section of the catheter has a durometer of about 40 D.

17. An implant device deployment system as defined in claim 15, wherein the implant device is comprised of a helical coil having a proximal end, a distal end and a lumen extending therethrough, a seal plug is disposed in fluid-tight engagement within the lumen at the proximal end of the coil and the proximal end of the coil is disposed within the lumen of the distal section of the catheter.

18. An implant device deployment system as defined in claim 15, wherein said proximal section of said catheter is formed of a polymer having a durometer in a range of 62 D to 75 D.

19. An implant device deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure is applied to the lumen of the catheter the walls of the distal section of the catheter expand outwardly;

an implant device being disposed in fluid-tight engagement within the lumen of the distal section of the catheter; and, a connector coupled to the proximal section of the catheter adapted to be connected to a source of fluid pressure which when applied through the connector to the lumen of the catheter causes the distal section of the catheter to expand outwardly to thereby release the implant device.

20. An implant device deployment system as defined in claim 19, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the catheter, the distal section is formed of a material which is also sufficiently flexible to be passed through the vasculature of the body and is of a durometer which is substantially lower than the durometer of the proximal section.

21. An implant device deployment system as defined in claim 20, wherein the distal section of the catheter is formed of a polymer having a durometer in a range of between about 25 D and 55 D.

22. An implant device deployment system as defined in claim 20, wherein the distal section of the catheter has a durometer of about 40 D.

23. An implant device deployment system as defined in claim 21, wherein said proximal section of said catheter is formed of a polymer having a durometer in a range of 62 D to 75 D.

* * * * *